United States Patent

Preiss et al.

[11] Patent Number: 5,911,871
[45] Date of Patent: Jun. 15, 1999

[54] PROCESS AND DEVICE FOR DETERMINATION OF PARAMETERS OF PARTICLES IN ELECTROLYTES

[75] Inventors: Willi Preiss, Eichstruth; Dieter Beckmann, Heiligenstadt, both of Germany

[73] Assignee: Institut Fur Bioprozess-und Analysenmesstechnik EV, Rosenhof, Germany

[21] Appl. No.: 08/779,261

[22] Filed: Jan. 6, 1997

[30] Foreign Application Priority Data

Jan. 5, 1996 [DE] Germany ............ 196 01 054

[51] Int. Cl.$^6$ .................................... G01N 27/26
[52] U.S. Cl. .............. 205/775; 204/400; 210/748
[58] Field of Search ............. 210/748; 204/409, 204/403, 400; 205/775, 792; 209/127.1, 127.4

[56] References Cited

U.S. PATENT DOCUMENTS 5,376,878 12/1994 Fisher ......................... 324/71.4

FOREIGN PATENT DOCUMENTS

2145531C2 3/1973 Germany .
3626600A1 3/1987 Germany .
06174630 6/1994 Japan .

OTHER PUBLICATIONS

JAPIO abstract JP 06174630 (Kazuo et al.), Jun. 24, 1994.
R. Thom et al., "Die elektronische Volumenbestimmung von Blutkörperchen und ihre Fehlerquellen," Z. ges.exp. Med. 151, 331–349 (1969), pp. 331–349. month unknown.

Primary Examiner—Elizabeth McKane
Assistant Examiner—Alex Noguerola
Attorney, Agent, or Firm—Christie, Parker & Hale, LLP

[57] ABSTRACT

The invention concerns a process and a device for the determination of parameters of particles in electrolytes, in particular of biological particles, whereby the particles to be measured are flushed through a measure pore which consists of a multilayer system. The process is characterized in that the particles are alternatingly exposed to different electrical potentials during the passage and that the signals obtained due to the interaction of the different potentials with the particles are then combined with each other. Preferably, the signals measured with a temporal offset are combined so that the resulting signals have different signs. The device has a measurement pore made up of a multilayer system, whereby electrically conducting and nonconducting layers are disposed alternatingly and whereby the measurement pore runs crosswise through the various layers.

12 Claims, 4 Drawing Sheets

PROCESS AND DEVICE FOR DETERMINATION OF PARAMETERS OF PARTICLES IN ELECTROLYTES

FIELD OF THE INVENTION

The present invention relates to a process and device for determining the parameters of particles in electrolytes, and more particularly, to a process and device for determining the parameters of particles in electrolytes using a measurement pore.

BACKGROUND OF THE INVENTION

Various processes are known for the determination of physical and biochemical parameters of particles, such as microorganisms or cells, in electrolytes. These electrolytes experience a change in resistance induced by a particle in a measurement pore as a result of the displacement of the electrolytes. (Thom, R., et al., "The electronic volume determination of blood solids and sources of errors therein;" Z. ges. exp. Med. 151,331–349/1969). Accordingly, prior art devices typically perform amplitude measurement according to Coulter, wherein only the maximum amplitude of a pulse is used, as well as pulse width, in which the pulse width is evaluated as a measure of the particle volume.

In both processes, measurement pores of monocrystalline structures are used, e.g., watch jewels, which for reasons of stability and measurement technology have a length to diameter ratio of virtually one to one. In measurement pores for small particles, the pore length must, for the stability reasons mentioned, be at least equal to the diameter, since otherwise with the conical opening, the remaining wall thickness, which corresponds to the capillary length, becomes unstable. In measurement pores for large particles, i.e., from 45 $\mu$m, the pore length must be equal to or greater than the diameter of the particle so that the particle is completely taken in by the pore during measurement to prevent measurement errors.

In the prior art devices the measurement pore is disposed between two electrodes whose distance from the measurement pore is a multiple of the length of the measurement pore (German Pat. No. 21 45 531 C2). This distance is up to 100 times the length of the measurement pore.

From German Pat. No. 36 26 600 A1, a device for determining the properties of particles suspended in liquids is known. This device has, as a measurement pore, a channel which runs through a material produced by using multilayer bonding technology. This results in a plurality of layers of material which are inseparably bonded to each other. Thus, it is possible to produce the channel with a gradually altered cross section.

The disadvantage of the process using the prior art measurement pores is that, for stability reasons, capillary lengths of less than 40 $\mu$m cannot be stably produced with the known techniques for processing monocrystalline structures and are mechanically unstable in use. At the lower measurement limit, the limit is a function of the ratio of the displaced volume to the entire volume inside the measurement pore. When there is a large volume of the measurement pore along with a small particle volume, the relative change in resistance is low and delivers no usable measurement results. Consequently, only large particles are measurable.

It is known that there must always be only one particle inside the measurement pore, since otherwise there would be erroneous measurements relative to the particle number and size. Due to the large volume of the measurement pore, that is not completely guaranteed, i.e., the coincidence limit is relatively low. Consequently, with high particle concentrations, high rates of dilution before the measurement are essential.

Since the electrodes may only be placed at the aforementioned large distance from the measurement pore, a nonhomogeneous electrical field is produced in front of the pore. As a result, large particles cause a change in electrical resistance at a long distance in front of the pore and consequently broaden of the pulse. This then causes errors in the pulse surface analysis and additional coincidence errors.

A further disadvantage is that the measurement process cannot be performed on-line. This is because there is a high sensitivity to external electromagnet radiations, since one side of the measurement pore may be at ground potential, whereas the other side is linked to the input of the amplifier which acts as an antenna.

Moreover, the measurement signal is a function of the volume, only not of the shape of the particles. However, the shape is of great interest in various applications, e.g., in biological measurements of cells.

In the prior art measurement processes, there is a cubic relationship between diameters of the particles and the amplitude of the measurement pulse, which results in a very small dynamic range of the measurement process. Thus, for example, with a desired resolution of 0.05 $\mu$m (diameter of the particle) at a lower measurement limit of 1 $\mu$m, there is a maximum dynamic range of 1:3.5 with an 8-bit resolution of the measurement signal.

Another disadvantage is due to the high internal resistance of the capillary. The noise voltage of the measurement arrangement is increased by the high internal resistance, which is proportional to the root of the internal resistance. This noise voltage also restricts the shifting of the measurement limit in the direction of smaller particles.

In the aforementioned processes, only simple resistance measurements are performed which produce information concerning only the physical parameters. If information is also needed with regard to the biochemical behavior of microorganisms or cells in their interior or on their surface, these investigations must be carried out using expensive preparation techniques (micromanipulators or microelectrodes, patch-clamp technique) as well as simple resistance measurements.

SUMMARY OF THE INVENTION

The object of the invention is to enable a simpler, more accurate determination of physical and, for biological particles, biochemical parameters of particles, whereby the size range of the particles to be measured is expanded.

In accordance with an embodiment of the present invention, a multilayer system having a measurement pore and electrically conducting and nonconducting layers alternately disposed is used to determine the parameters of particles in electrolytes. The measurement pore extends crosswise through the multilayer.

The method for determining the parameters of particles in an embodiment of the present invention includes passing the particles through the measurement pore, alternately exposing the particles to different electrical potentials as the particles are passed through the measurement pore, and combining signals resulting from the interaction of the different potentials with the particles.

Preferably, the signals measured, which are temporally offset from each other, are combined such that the resulting signals have different polarities. Signals thus combined result in improved signal to noise ratios.

In another embodiment of the process, the difference in travel time of the particles between the different potentials is measured with a constant flow rate of the electrolyte. In conjunction with the aforementioned combination of signals, this enables determination of the length of the particle in addition to the doubling of the amplitude of the measurement signal. With this process, it is possible to trigger the entire measurement signal with the first signal measured.

An arrangement for the determination of parameters of particles in electrolytes, in particular of biological particles, has a measurement pore which is made up of multilayer systems, whereby electrically conducting and nonconducting layers are disposed alternatingly and whereby the measurement pore runs crosswise and preferably perpendicular to the various layers. Preferably, at least one conducting layer simultaneously acts at a measurement electrode.

The thickness of the layers is in the micron range and is preferably $1/10$ to $1/1000$ of the diameter of microorganism.

This arrangement has the advantage that, as a result of the use of the conducting layers constituting the measurement pore as measurement electrodes, external electrodes may be eliminated, whereby there is a more homogeneous electrical field and, consequently, smaller measurement errors and improved coincidence. Moreover, this arrangement has a lower internal resistance whereby the measurement limit shifts in the direction of smaller particles. The measurement signal is also now dependent only on the cross section of the particle and no longer on its volume, whereby greater dynamic range is possible.

This arrangement also has the advantage that, as a result of the layered structure, production using modern production techniques, such as semiconductor technology or microsystem technology, is possible. Thus, high production consistency, low tolerances, and low costs are ensured. Moreover, easier establishment of the contacts of the measurement electrodes is possible, and improved mechanical stability of the device is obtained.

Due to these improved properties, it is now possible to expand the area of application of measurement pores both in the direction of smaller and of larger particles, e.g., to bacteria, technical dusts, or large cells.

In one embodiment, the thickness of the nonconducting layers is less than the particle size. Thus, a diskwise scanning of the particle is possible and with it the determination of length, diameter, and volume during passage of the particle through the measurement pore. Through this diskwise or tomographic analysis, the determination of the shape of the particle is possible.

Another advantageous embodiment of the invention provides that both outer layers are grounded. Thus, susceptibility to interference is further reduced, and the device may be used online in a technical system.

In another embodiment provision is made upstream in the flow direction before the layers to provide an electrically conducting hollow cylinder which runs concentric with the measurement pore and is insulated from it by an electrically nonconducting layer. Thus, upon connection with an electrical voltage between the next electrically conducting layer and the electrically conducting cylinder, an electrical field is formed so that the electrolyte flowing through the measurement pore, which is the carrier for the particles, is deflected toward the wall of the measurement pore and decelerated there so that from the wall to the center of the measurement pore, there is a speed gradient of the flow, and thus the center of the pore effects an electronic focusing on the nonconducting particle to be measured.

In the prior art processes and devices, it was possible to use only simple resistance measurements for the analysis of biological objects, whereby in separate devices and process steps either a geometric measurement or information concerning biological behavior could be obtained through the use of expensive preparation techniques. With the process and the device according to the invention, on-line impedance measurements on biological objects are now possible in a simple manner. It is known that impedance measurements in the three dispersion areas ($\alpha,\beta,\delta$), i.e., in the kHz to GHz frequency range, yield information concerning the biochemical behavior of biological objects, such as microorganisms or cells, in their interior or on their surface. For the first time, geometrical and biochemical measurement of particles is possible in one device, without special preparation.

The invention is explained in detail in exemplary embodiments with reference to the drawings.

BRIEF DESCRIPTION OF THE DRAWINGS

FIG. 3b a block diagram with an amplifier for the measurement pore according to FIG. 3a;

FIG. 4b is a block diagram with amplifier for the measurement pore according to FIG. 4a.

DETAILED DESCRIPTION

Figure 1:
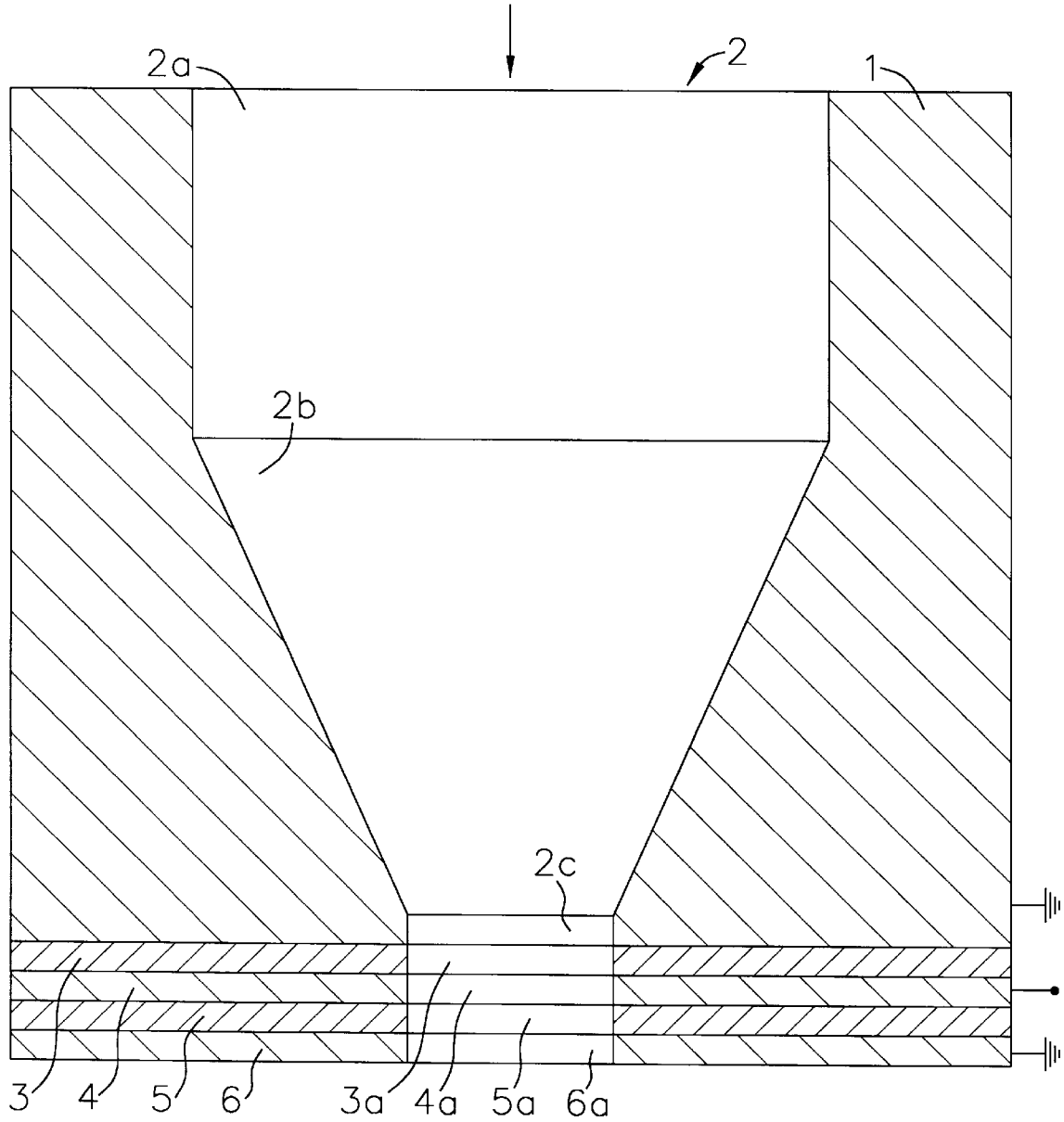
FIG. 1 is a measurement pore in a first embodiment.

The measurement pore according to FIG. 1 consists of a main body 1 made of conducting material, which has a passage 2 comprising a cylindrical section 2a connected to a narrowing conic section 2b connecting. Another cylindrical section 2c, whose cross section is smaller than that of the cylindrical section 2a is connected to conic section 2b. On this side of the main body, nonconducting layers 3 and 5 are provided alternating with conducting layers 4,6. These layers are, for example, applied using semiconductor technology or microsystem technology, for example, by sputtering or by plasma spraying. Layers 3 through 6 have passages 3a,4a,5a, and 6a, which have the same cross section as the section 2c of the passage 2. Together the passages form the measurement pore.

The main body 1 and the conducting layer 6 are at ground potential. The conducting layer 4 serves as the measurement electrode. The particle to be analyzed enters the measurement pore in section 2a and passes in succession through the conducting main body 1, the nonconducting layer 3, the conducting layer 4, the nonconducting layer 5, and the conducting layer 6.

Figure 3A:
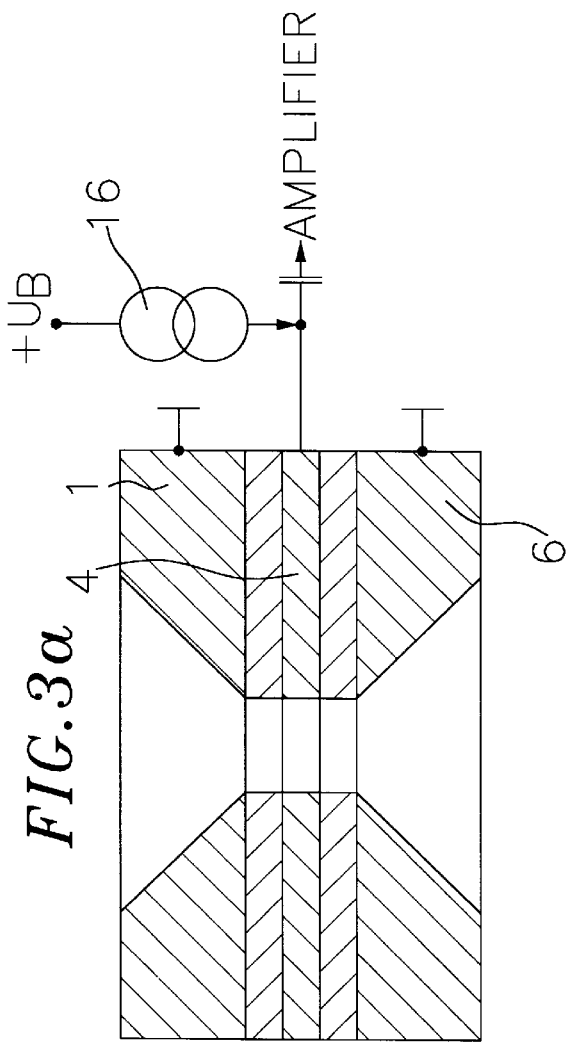
FIG. 3a is a measurement pore with a current source connected to the measurement electrode for signal pickup.
Figure 3B:
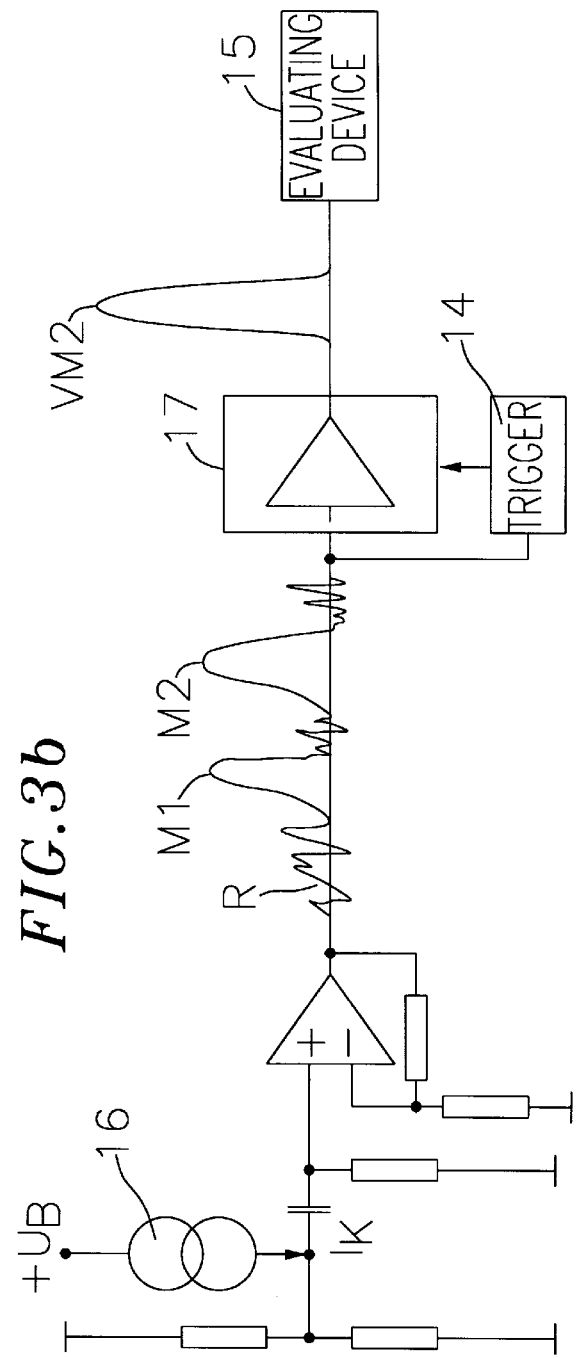

An embodiment of a circuit for use with the measurement pore is depicted in FIG. 3a and 3b. A current source 16 is linked with the conducting layer 4. Two positive measurement signals M1 and M2 are generated with an interval of time between them. The first measurement signal M1 is used for time-delayed triggering of the second measurement signal by means of a trigger 14. After amplification with an amplifier 17, an amplified second measurement signal M2 is obtained, whereby the noise R previously present was eliminated. The measurement results are evaluated by an evaluating device 15 connected to the output of the amplifier 17.

Figure 4A:
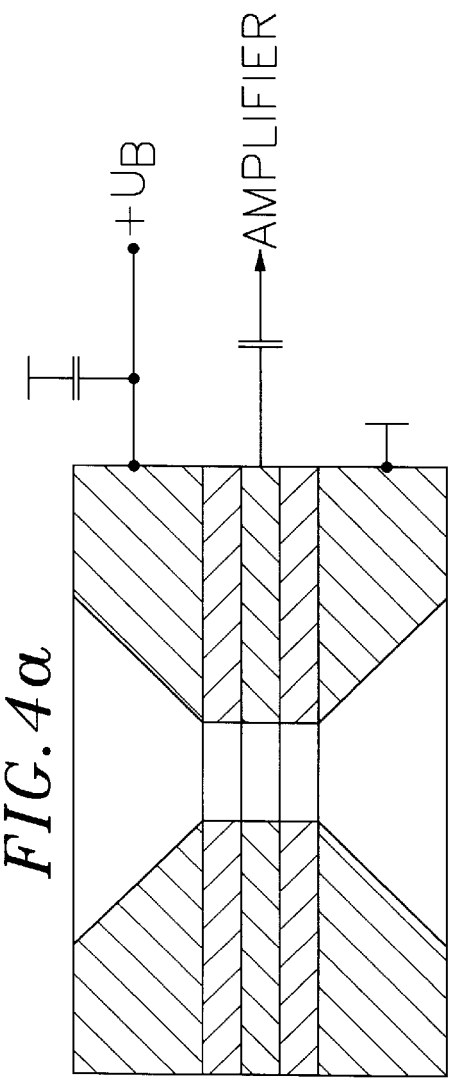
FIG. 4a is a measurement pore with a voltage source lying on its conducting main body for signal pickup.
Figure 4B:
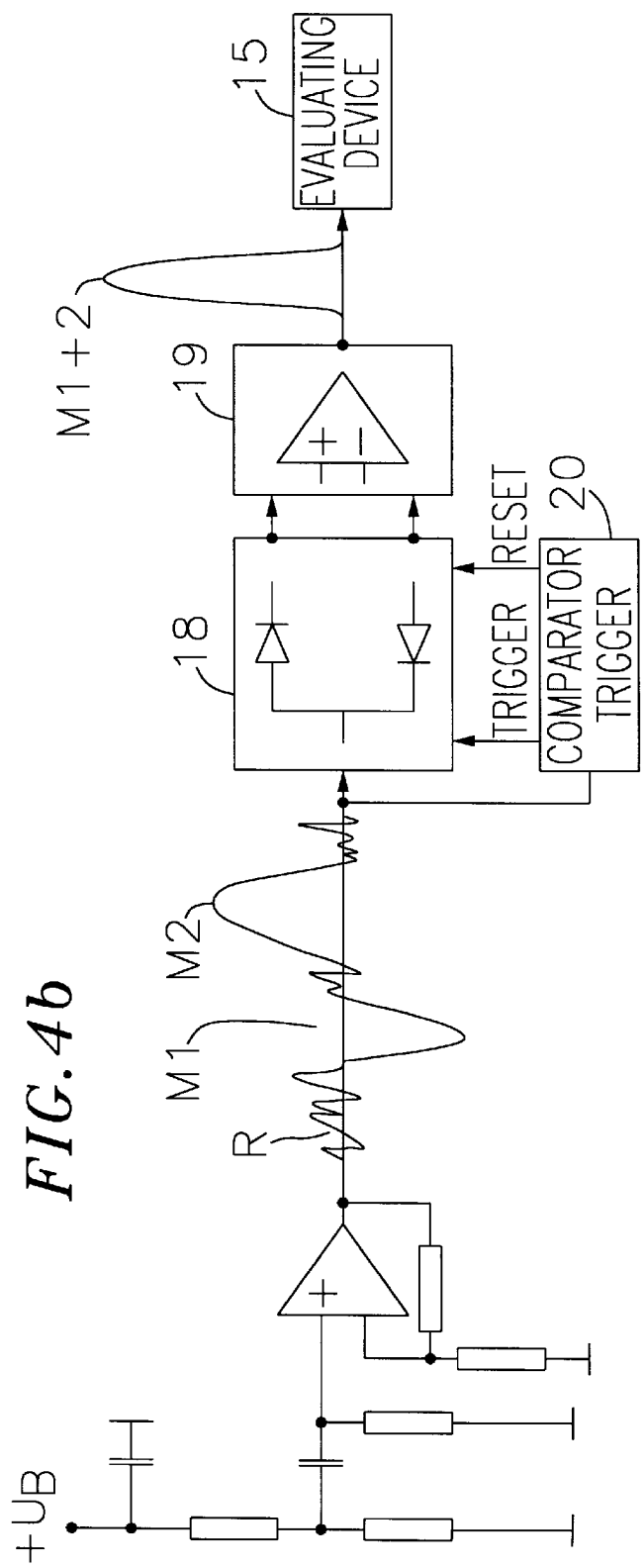

An alternative embodiment of a circuit for use with the measurement pore is depicted in FIGS. 4a and 4b. A voltage source is connected to the measurement pore. Using this circuit a negative first measurement signal M1 and a positive second measurement signal M2 are generated. By means of a rectifier 18 for peak value rectification and a differential amplifier 19, a measurement signal M1+2 is formed, which represents the sum of the negative first measurement signal M1 and the positive second measurement signal M2, whereby the noise R is also eliminated by measured value processing using this circuit. In this process, the leading edge of the negative first measurement signal M1 triggers the rectifier 18 when the negative first measurement signal M1 falls below a threshold voltage established by a comparator 20. The trailing edge of the positive second measurement signal M2 resets the rectifier 18 when the positive second measurement signal M2 falls below a second threshold voltage established by the comparator 20. However, a reset may also occur after a specific time interval.

Figure 2:
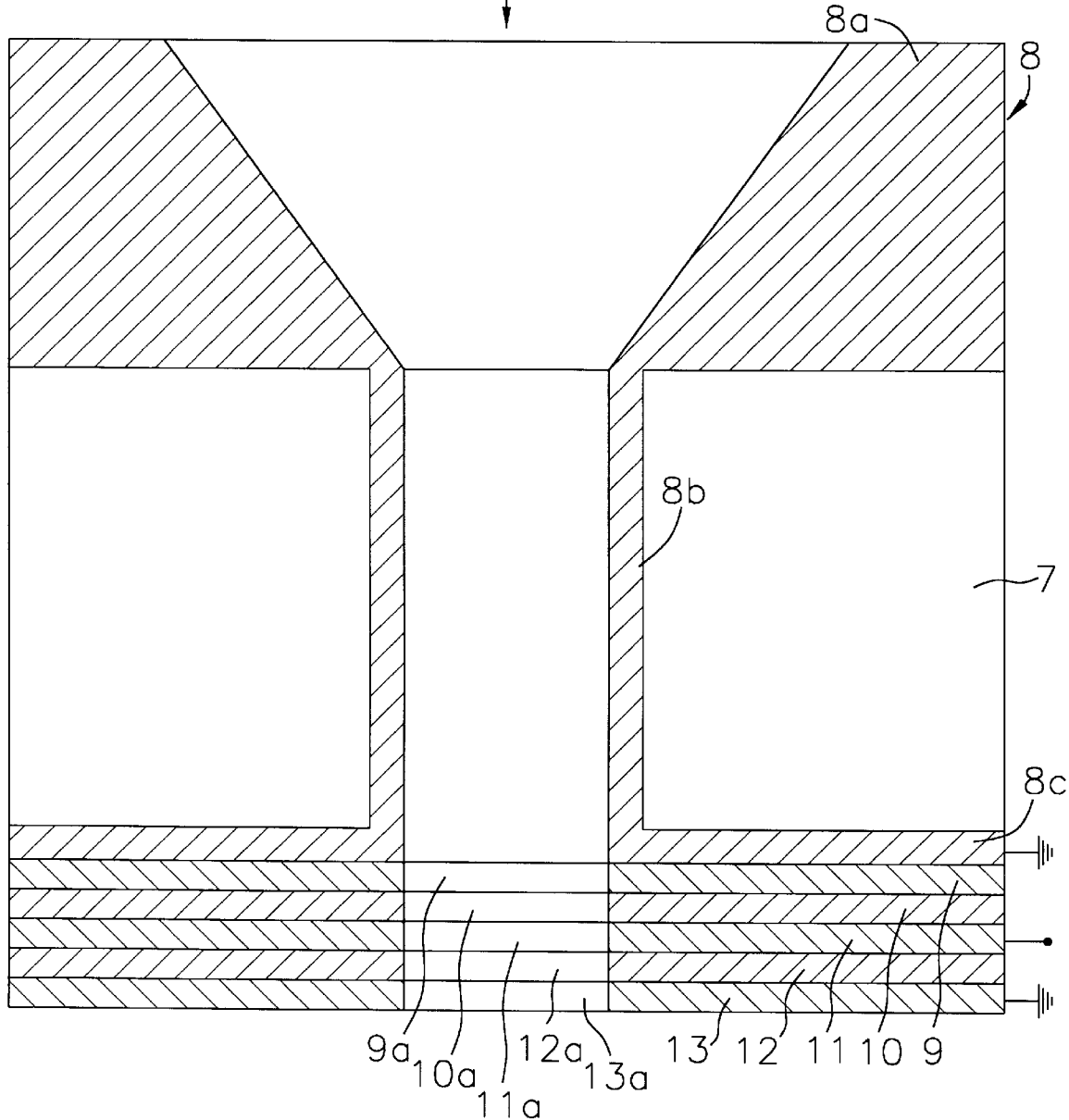
FIG. 2 is a measurement pore with an additional electrically conducting cylinder.

In the embodiment in FIG. 2, a measurement pore is depicted whereby an electrically conducting cylinder 7 is provided, which is disposed concentrically with the measurement pore viewed from upstream before the measurement layers. The cylinder 7 is disposed in an electrically nonconducting molded body 8, which insulates the cylinder from the measurement pore. The molded body 8 has a section 8a with a conic passage for the particles to be measured, to which a hollow section 8b connects. The hollow section 8b is connected to a layered section 8c.

Electrically conducting layers 9, 11, 13 and nonconducting layers 10, 12 are connected to the layered section 8c. The layers 9 and 13 are at ground potential, and the layer 11 serves as a measurement electrode. These sections 9 through 13 are provided with passages 9a through 13a, which have the same diameter as the section 8b.

The application of an electrical voltage between the cylinder 7 and the electrically conducting layer 9 creates an electrical field causing the electrolyte flowing through the measurement pore, which is the carrier for the particles to be measured, to be deflected to the wall of the measurement pore and decelerated there. Thus, there is, from the wall to the center of the measurement pore, a speed gradient of the flow, and thus the center of the pore effects. Thus, an electronic focusing on the nonconducting particles to be measured.

What is claimed is:

1. A method for determining the parameters of particles in electrolytes using a measurement pore, said measurement pore extending crosswise through a multi-layer system having alternately disposed electrically conducting and nonconducting layers with different electrical potentials applied to the electrically conducting layers, said method comprising the steps of:

passing electrolytes comprising the particles through the measurement pore;

alternately exposing the particles to different electrical potentials as the particles are passed through the measurement pore;

combining signals resulting from the interaction of the different potentials with the particles; and determining the parameters of the particles in the electrolyte as a function of said combined signals.

2. The method of claim 1 wherein the combined signals comprises two signals having different polarities, and the combining step further comprises the step of measuring said two signals at a temporal offset, and combining the two measurements.

3. The method of claim 2 wherein the combining step is triggered by one of the two measured signals.

4. The method of claim 1 or 2 wherein the electrolytes have a constant flow speed, and further comprising the step of measuring the passage time difference of the particles between the different potentials.

5. The method of claim 4 wherein the combining step is triggered by one of the two measured signals.

6. A device for determining the parameters of particles in electrolytes, comprising:

a multi-layer system having a measurement pore, and electrically conducting and non-conducting layers alternately disposed, the measurement pore extending crosswise through the multi-layers; and means for providing different electrical potentials to the electrically conducting layers.

7. The device according to claim 6 wherein the measurement pore extends perpendicular to the multilayers.

8. The device according to claim 6 or 7 further comprising a current source connected to one of the conducting layers.

9. The device according to claim 6 or 7 further comprising the electrolytes with the particles disposed in the measurement pore, and wherein the thickness of the nonconducting layers is less than the size of the particles.

10. The device according to claim 6 or 7 further comprising an electrically conducting hollow cylinder concentric with the measurement pore, said cylinder having an electrically nonconducting layer for insulation from the measurement pore.

11. A device for determining the parameters of particles in electrolytes, comprising a multilayer system having electrically conducting and nonconducting layers alternately disposed, said electrically conducting layers comprising two conducting outer layers, said two outer conducting layers being grounded, and a measurement pore extending crosswise through said multilayer system.

12. The device according to claim 6 or 7 further comprising a voltage source connected to one of the conducting layers.

* * * * *